(12) United States Patent
Mindich

(10) Patent No.: US 11,540,816 B2
(45) Date of Patent: Jan. 3, 2023

(54) SYSTEM FOR PREPARING A HARVESTED BLOOD VESSEL FOR GRAFTING

(71) Applicant: Bruce Mindich, Chappaqua, NY (US)

(72) Inventor: Bruce Mindich, Chappaqua, NY (US)

(*) Notice: Subject to any disclaimer, the term of this patent is extended or adjusted under 35 U.S.C. 154(b) by 470 days.

(21) Appl. No.: 16/820,989

(22) Filed: Mar. 17, 2020

(65) Prior Publication Data

US 2021/0290212 A1    Sep. 23, 2021

(51) Int. Cl.
*A61B 17/00* (2006.01)
*A61F 2/06* (2013.01)
*B25B 5/00* (2006.01)

(52) U.S. Cl.
CPC .......... *A61B 17/00008* (2013.01); *A61F 2/06* (2013.01); *A61F 2/062* (2013.01); *B25B 5/003* (2013.01); *B25B 5/006* (2013.01); *A61B 2017/00778* (2013.01)

(58) Field of Classification Search
CPC ..... A61B 17/00008; A61B 2017/00778; A61F 2/06; A61F 2/062; B25B 5/003; B25B 5/006
See application file for complete search history.

(56) References Cited

U.S. PATENT DOCUMENTS

| | | | | |
|---|---|---|---|---|
| 3,916,874 A | * | 11/1975 | Perrin | A61F 2/06 600/36 |
| 4,232,659 A | * | 11/1980 | Dale | A61F 2/06 600/36 |
| 5,397,357 A | * | 3/1995 | Schmieding | A61F 2/0811 606/86 R |
| 5,902,228 A | | 5/1999 | Schulsinger et al. | |
| 6,019,771 A | | 2/2000 | Bennett et al. | |
| 6,554,764 B1 | | 4/2003 | Vargas et al. | |
| 6,796,977 B2 | * | 9/2004 | Yap | A61F 2/08 606/88 |
| 6,821,286 B1 | | 11/2004 | Carranza et al. | |
| 8,123,672 B2 | * | 2/2012 | Viitala | A61F 2/062 600/36 |
| 2004/0186356 A1 | | 9/2004 | O'Malley et al. | |
| 2008/0027272 A1 | * | 1/2008 | Kadykowski | A61F 2/062 600/36 |
| 2009/0112053 A1 | | 4/2009 | Viitala et al. | |

FOREIGN PATENT DOCUMENTS

| | | |
|---|---|---|
| CN | 205181594 U | 4/2016 |
| JP | 2014-188376 A | 10/2014 |
| WO | 92-14419 A1 | 9/1992 |

OTHER PUBLICATIONS

Written Opinion and International Preliminary Report on Patentability issued in PCT/US2021/018241, dated Sep. 20, 2022.

* cited by examiner

*Primary Examiner* — Anita M King
(74) *Attorney, Agent, or Firm* — Locke Lord LLP; Scott D. Wofsy; Christopher J. Capelli

(57) ABSTRACT

A system for preparing a harvested blood vessel for use as a graft during a coronary artery bypass procedure, which includes an elongated platform, a mounting flange extending upwardly from a top surface of the platform adjacent a proximal end thereof for supporting a syringe in a fixed position, and a pair of longitudinally spaced apart clamp holders operatively associated with the top surface of the platform, each clamp holder configured to support a respective vessel clamp, wherein the vessel clamps supported within the clamp holders are adapted to hold a harvested blood vessel immobile therebetween so it can be prepared for grafting.

13 Claims, 5 Drawing Sheets

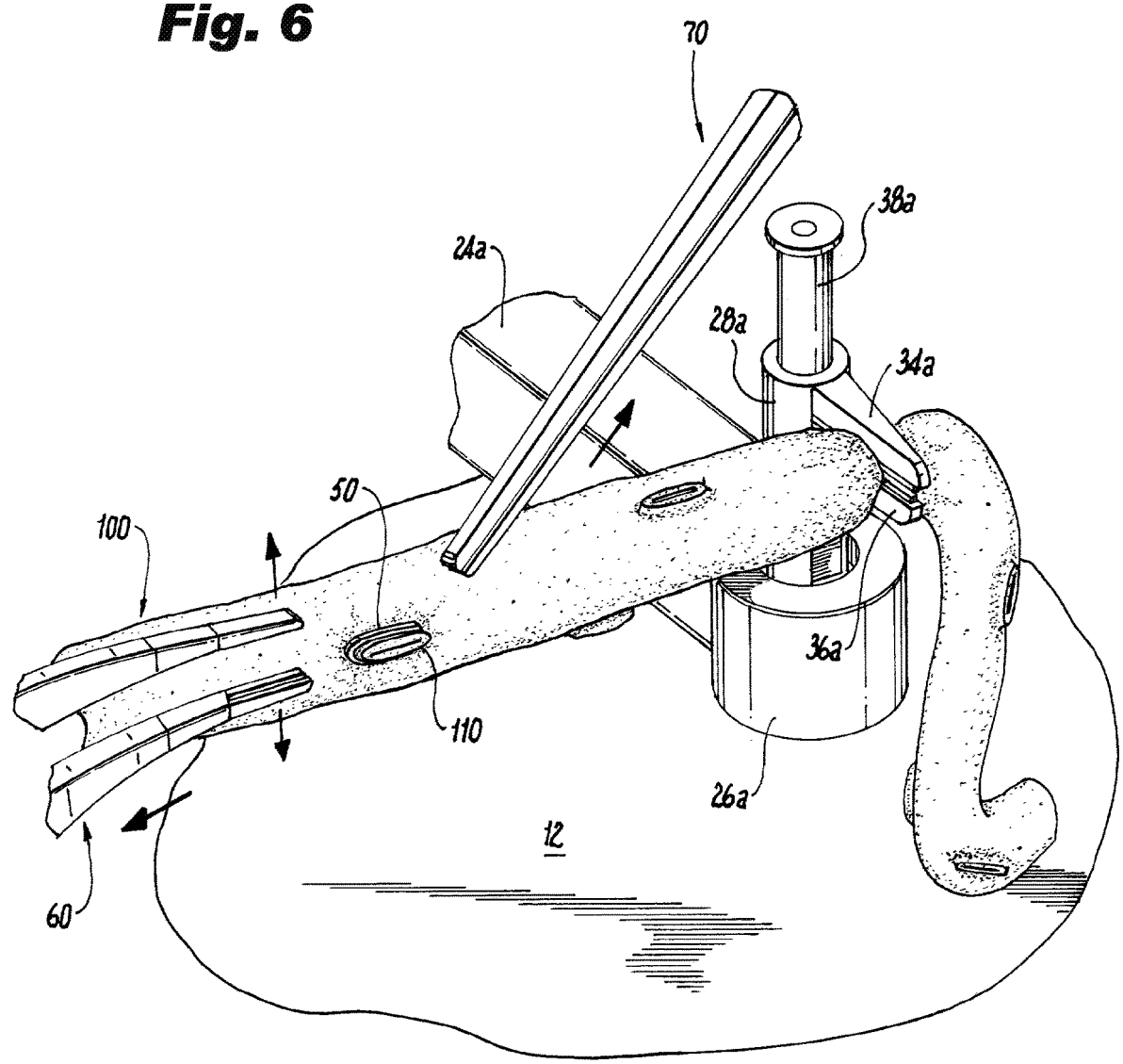

SYSTEM FOR PREPARING A HARVESTED BLOOD VESSEL FOR GRAFTING

BACKGROUND OF THE INVENTION

1. Field of the Invention

The subject invention is directed to vascular surgery, and more particularly, to a system and method for preparing a harvested blood vessel for grafting during a coronary artery bypass procedure.

2. Description of Related Art

During coronary artery bypass surgery, saphenous vein and radial arteries are frequently harvested from a patient and then utilized for bypassing diseased coronary arteries. This is typically done using endoscopic methods to reduce patient trauma. During removal, the side branches of the blood vessel are divided, and the end that remains in the patient is cauterized to prevent bleeding.

Once it has been harvested, the blood vessel is prepared for use as a graft. That is, the side branches must be permanently closed to prevent bleeding under arterial pressure. This typically requires ligation or clipping of the side branch openings and repair of any holes in the conduit. Usually, this is done by the surgeon who has removed the blood vessel from the patient. It is however, a cumbersome and time consuming task when performed by one person.

Given the constraints on available personnel in an operating room, an assistant often unavailable during the procedure. Moreover, if the surgeon harvests the vessel and then prepares it for grafting with an assistant, the flow of the operation is halted, which is both time consuming and costly. Thus, there is a need in the art for a system and method to reduce the time and cost associated with preparing a harvested blood vessel for grafting during a coronary artery bypass procedure. The subject invention present such a solution.

SUMMARY OF THE DISCLOSURE

The subject invention is directed to a new and useful system for preparing a harvested blood vessel or conduit for grafting during a coronary artery bypass procedure. The conduit preparation system includes an elongated platform, a mounting flange extending upwardly from a top surface of the platform adjacent a proximal end thereof for supporting a syringe in a fixed position, and first and second longitudinally spaced apart clamp holders that are operatively associated with the top surface of the platform.

Each clamp holder is configured to support a respective vessel clamp, wherein the vessel clamps supported within the clamp holders are adapted to hold a harvested blood vessel immobile therebetween. This provides temporary occlusion of the blood vessel after it has been inflated by a fluid from the syringe to allow for distension of the blood vessel so it can be evaluated and prepared for grafting.

The system also includes a syringe that is supported by the mounting flange for delivering the fluid into a proximal end of the blood vessel held between the vessel clamps to inflate the blood vessel. The mounting flange includes a reception slot and the system further comprises a funnel that is attached to a distal end of the syringe for engagement with the reception slot.

Preferably, the first and second longitudinally spaced apart clamp holders are mounted for tandem movement within an elongated channel extending along the platform between the opposed proximal and distal end portions thereof. The clamp holders are supported on an elongated beam that is mounted for longitudinal sliding movement relative to the platform within the elongated channel. Each clamp holder includes an arm that extends laterally outward from the elongated beam and includes a rounded socket for receiving and retaining a respective vessel clamp. Each vessel clamp is a spring loaded bulldog clamp configured for reception within the socket of a clamp holder. Each clamp holder has an associated fastener for retaining the vessel clamp within the socket thereof.

The subject invention is also directed a system for preparing a harvested blood vessel for grafting, which includes an elongated platform, a mounting flange extending upwardly from a top surface of the platform adjacent a proximal end thereof for supporting a syringe in a fixed position, a syringe configured to be supported by the mounting flange for delivering fluid into a proximal end of the blood vessel, a pair of longitudinally spaced apart clamp holders operatively associated with the top surface of the platform, and a vessel clamp supported within each clamp holder for holding a harvested blood vessel immobile therebetween, providing temporary occlusion of the blood vessel after it has been inflated by a fluid from the syringe to allow for distention of the blood vessel so it can be prepared for grafting.

The subject invention is also directed to a method for preparing a harvested blood vessel for grafting, which includes the steps of harvesting a blood vessel from a patient, distending the blood vessel, immobilizing the distended blood vessel between two longitudinally spaced apart vessel clamps to temporarily occlude an elongated section of the blood vessel, and repairing defects in the elongated section of the immobilized and distended blood vessel.

Preferably, the step of distending the blood vessel involves inflating the blood vessel with a fluid, and the step of repairing defects involves closing side branch openings in the elongated section of the blood vessel to prevent bleeding under arterial pressure. This can be done by applying a hemostatic clip to a defect or by using a suture to repair a defect.

These and other features of the conduit preparation system and method of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the conduit preparation system of the subject invention without undue experimentation, preferred embodiments thereof will be described in detail herein below with reference to the figures wherein:

FIG. 6 is an enlarged localized view from FIG. 1 illustrating the application of a hemostatic clip to the harvested blood vessel to repair a defect therein.

DETAILED DESCRIPTION OF THE PREFERRED EMBODIMENTS

Figure 1:
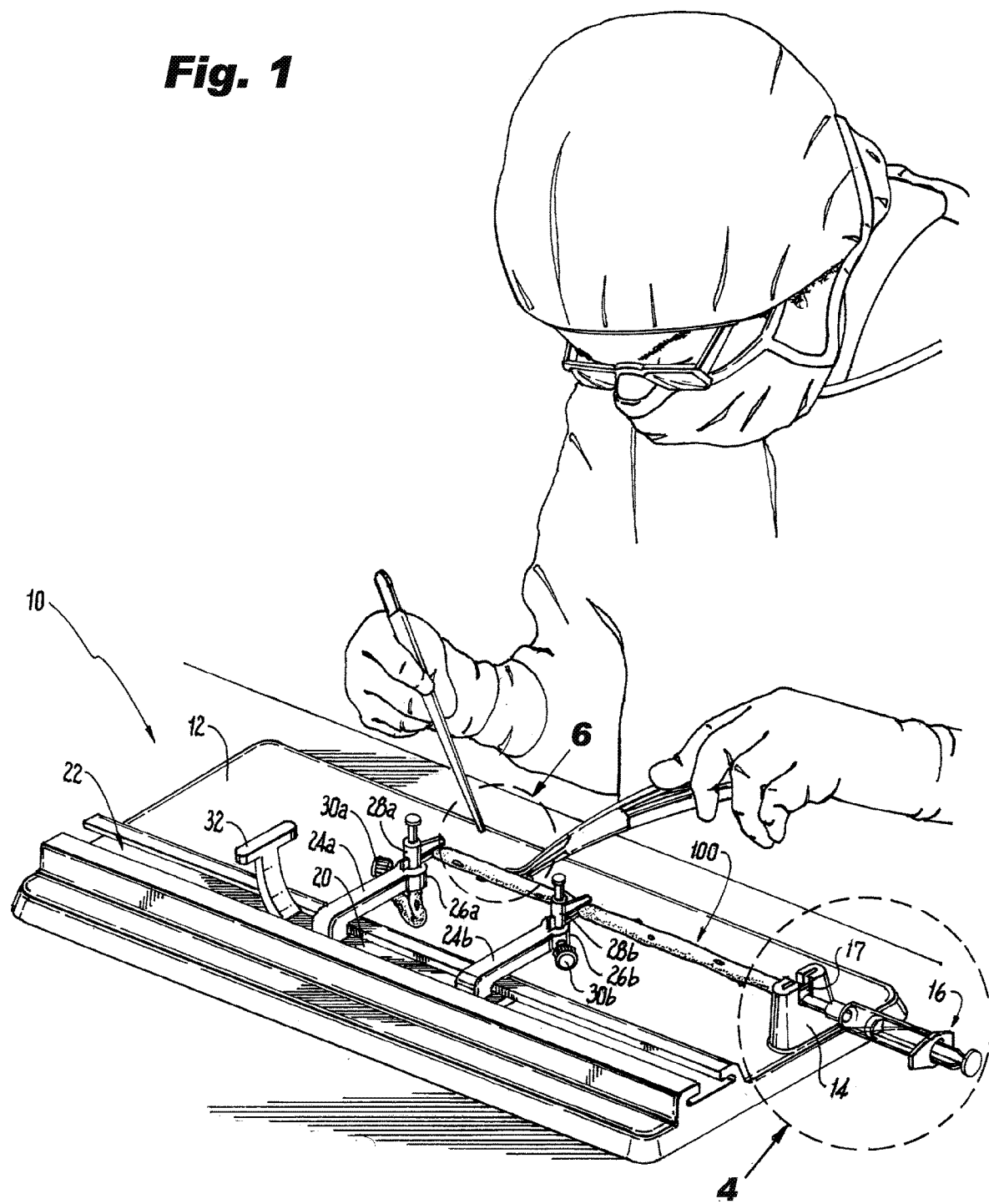
FIG. 1 is a perspective view of the conduit preparation system of the subject invention in use with a section of a harvested blood vessel immobilized and distended between two longitudinally spaced apart vessel clamps, which temporarily occlude the blood vessel so that the surgeon is able to use both hands to evaluate and repair defects in the blood vessel.

Referring now to the drawings, wherein like reference numerals identify similar structural elements and features of the subject invention, there is illustrated in FIG. 1 a system for preparing a harvested blood vessel or conduit, such as, for example, a saphenous vein or radial artery, for grafting during a coronary artery bypass procedure. The conduit preparation system of the subject invention is designed to enable a surgeon to prepare a harvested blood vessel for grafting using both hands and without an assistant, and to do so in an efficient and accurate manner, saving both time and expense in the performance of a coronary artery bypass procedure.

Figure 2:
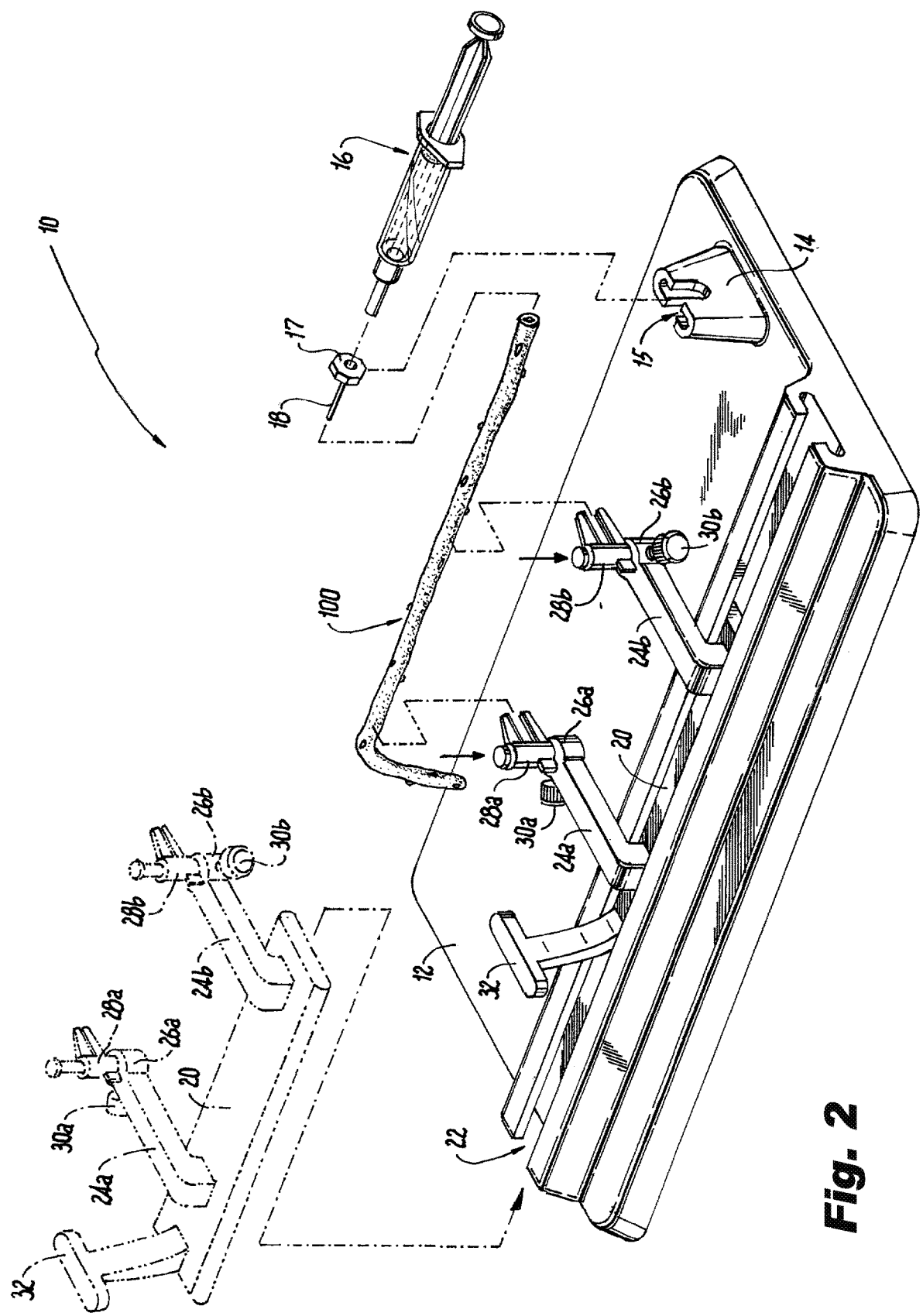
FIG. 2 is a perspective view of the conduit preparation system of the subject invention with the syringe separated from the mounting flange and showing the elongated beam and clamp holders in phantom separated from the elongated channel within which it slides.

Referring to FIG. 2, the conduit preparation system of the subject invention, which is designated generally by reference numeral 10, includes an elongated, generally rectangular platform 12 having opposed proximal and distal end portions. The elongated platform 12 can be fabricated from a medical grade stainless steel or a similar metallic material that can be readily cleaned and sterilized after use, or it could be constructed from a less expensive medical grade plastic material such as Lexan® brand material or a similar material, so that it can be more easily manufactured and discarded after a single use.

Figure 4:
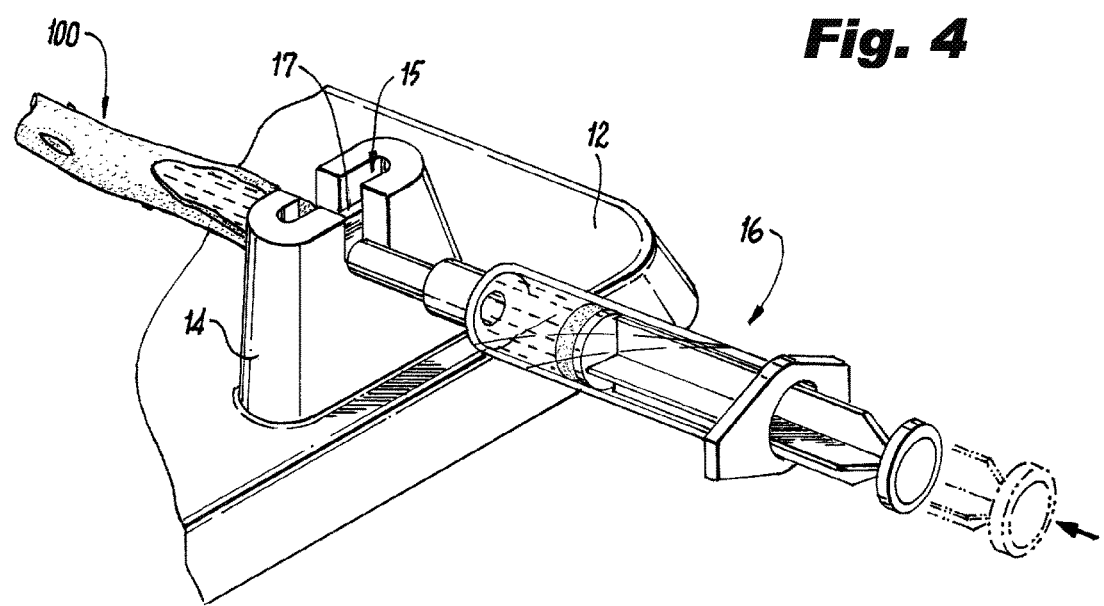
FIG. 4 is an enlarged localized view from FIG. 1 illustrating the syringe inflating the blood vessel with a fluid.

A mounting flange 14 extends upwardly from a top surface of the platform 12 adjacent a proximal end thereof for supporting a conventional safety syringe 16 in a fixed position. More particularly, as best seen in FIG. 4, the conduit preparation system 10 includes an elongated funnel 18 that is attached to a distal end of the syringe 16 and the funnel 18 includes a polygonal shaped head portion 17 configured for engagement within a reception slot 15 formed in the mounting flange 14. The syringe 16 is provided to deliver a fluid (i.e., saline fluid) into a proximal end of a harvested blood vessel 100 to inflate the blood vessel so that it can be evaluated and prepared for grafting, as explained in more detail below.

With continuing reference to FIG. 2, the conduit preparation system 10 further includes an elongated rectangular beam 20 that is mounted for longitudinal sliding movement relative to the platform 12 within an elongated raised track or channel 22. The channel 22 is preferably formed integral with and extends along a lateral rear edge of the platform 12 from the proximal end thereof to the distal end thereof. A pair of longitudinally spaced apart clamp holders 24a and 24b extend laterally outward from the elongated beam 20 and they move in tandem with the beam 20 relative to the platform 12. A handle 32 is operatively associated with a distal end of the beam 20 for manually moving the beam 20 within the channel 22 relative to the platform 12.

Figure 3:
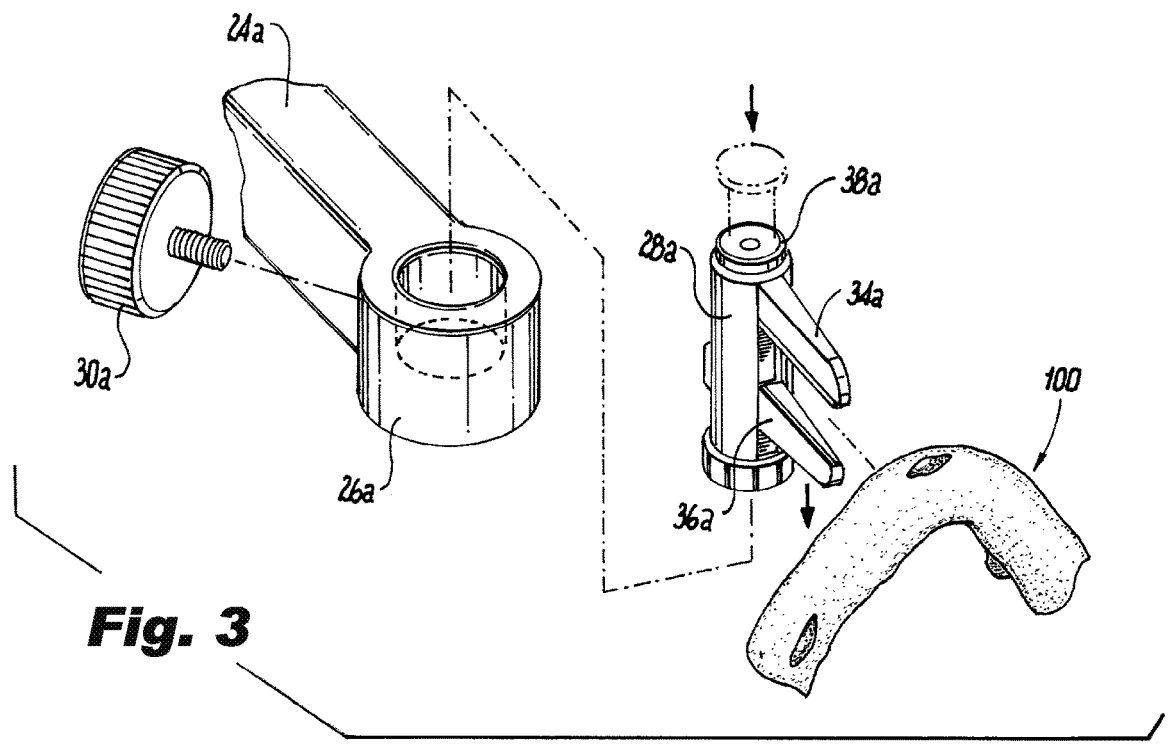
FIG. 3 is a perspective view of the socket at the end of a clamp holder with the spring loaded bulldog clamp and threaded fastener separated for ease of illustration.

Each clamp holder 24a, 24b is defined by a transverse arm that includes a rounded socket 26a, 26b at the free end thereof for receiving and retaining a respective vessel clamp 28a, 28b. The rounded socket 26a, 26b at the end of each clamp holder 24a, 24b has an associated threaded fastener or set screw 30a, 30b for releasably retaining the body portion of a vessel clamp 28a, 28b received therein, as best seen in FIG. 3. The threaded fasteners 30a, 30b also allow for angular or rotational adjustment of the vessel clamps 28a, 28b within their respective sockets 26a, 26b, as required by the surgeon.

The vessel clamps 28a, 28b are adapted to hold a section of a harvested blood vessel 100 immobile therebetween, so as to leave both hands of the surgeon free to prepare the blood vessel for grafting. The vessel clamps 28a, 28b also provide temporary occlusion of the harvested blood vessel 100 after it has been inflated by saline fluid from the syringe 16. This allows for distention of the blood vessel 100 to provide the surgeon with an opportunity to evaluate and repair any defects therein, as described in more detail below.

Preferably, each vessel clamps 28a, 28b is configured as a disposable spring loaded bulldog clamp, which is a conventional and universally available device. By way of example, with reference to FIG. 3, vessel clamp 28a includes a fixed upper jaw member 34a and a movable lower jaw member 36b. The lower jaw member 36b is operatively connected to a spring biased plunger 38a. In use, when the plunger 38a is depressed against the bias of an internal spring, the lower jaw 36b moves away from the upper jaw 34a, and when the plunger 38a is released, the lower jaw 36b moves back toward the fixed upper jaw 34a. Those skilled in the art will readily appreciate that other types of disposable vessel clamps are available in the marketplace and could be utilized with this system in place of the disposable bull dog clamps described and illustrated herein.

To use the conduit preparation system 10 of the subject invention, the funnel 18 that is provided at the distal end of the safety syringe 16 is inserted into the proximal end of a harvested blood vessel 100, such as for example, a section of saphenous vein harvested from the leg of a patient. Then, saline fluid from the syringe 16 is introduced into the blood vessel 100 through the funnel 18 to inflate the blood vessel, as illustrated in FIG. 4. A section of the harvested blood vessel 100 in then immobilized between the two longitudinally spaced apart vessel clamps 28a and 28b to temporarily occlude that section of the blood vessel 100, as shown in FIG. 1. Once again, this allows the surgeon to effectively evaluate any defects in the blood vessel that need to be repaired.

Figure 5:
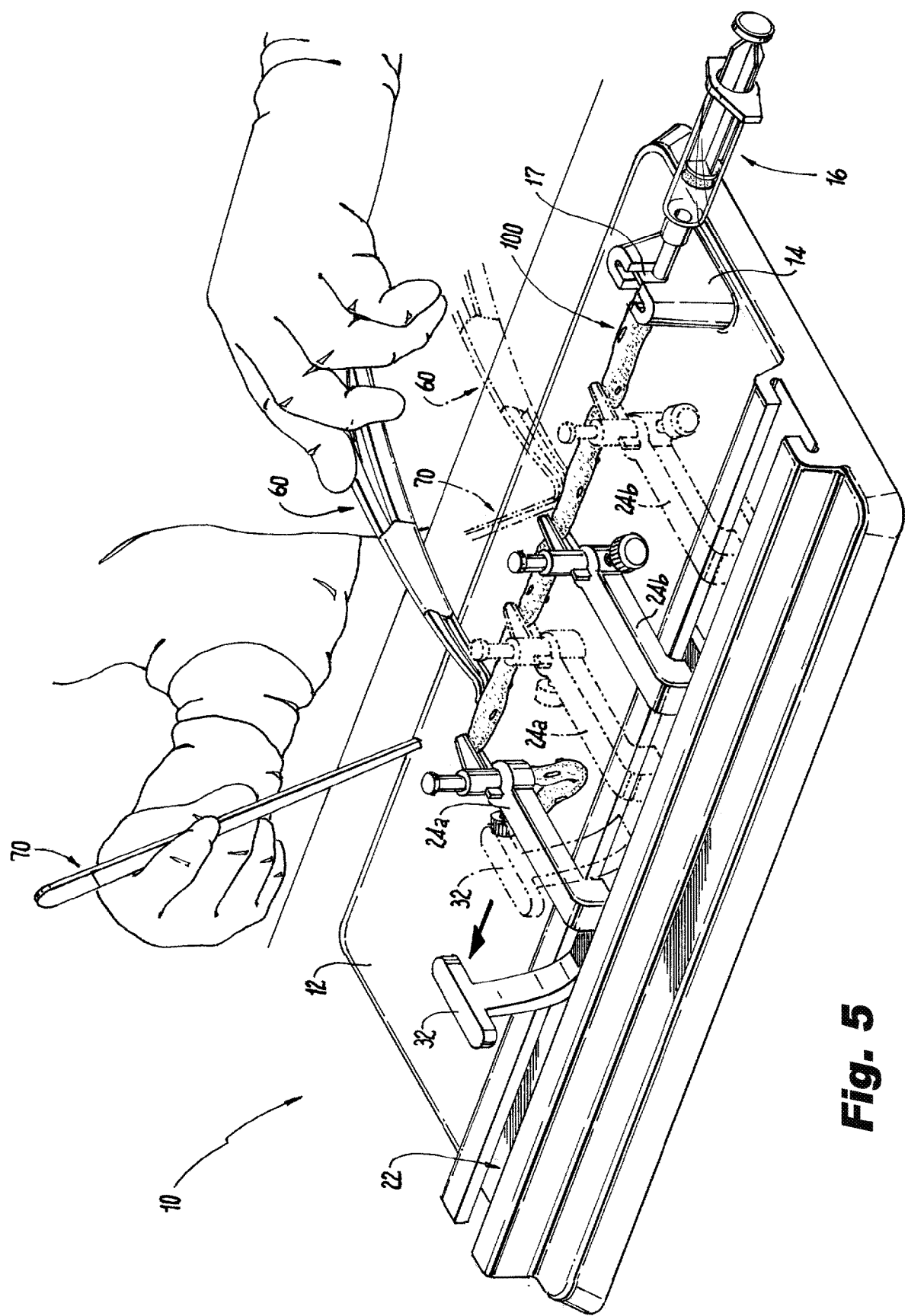
FIG. 5 is a perspective view of the conduit preparation system of the subject invention in use with a section of a harvested blood vessel immobilized and distended between two longitudinally spaced apart vessel clamps, illustrating sliding movement of vessel clamps in tandem relative to the platform.

Thereafter, as best seen in FIG. 6, using a clip applier 60 in one hand and a grasping tool 70 in the other, the surgeon can efficiently apply one or more hemostatic clips 50 to close off any side branch openings 110 or other defects in the immobilized and distended section of blood vessel 100. Alternatively, any openings or defects in the blood vessel can be repaired by a surgeon with sutures or ligatures using both hands. Once all of the defects or openings in the immobilized section of the blood vessel 100 have been repaired, the surgeon can release the blood vessel 100 from the two spaced apart vessel clamps 28a, 28b and manually reposition the beam 20 within the channel 22 in order to immobilize another section of the blood vessel 100 for repair, as illustrated in FIG. 5.

While the system and method of the subject disclosure have been shown and described with reference to preferred embodiments, those skilled in the art will readily appreciate that changes and/or modifications may be made thereto without departing from the scope of the subject disclosure.

What is claimed is:

1. A system for preparing a harvested blood vessel for grafting, comprising:
 a) an elongated platform;
 b) a mounting flange extending upwardly from a top surface of the platform adjacent a proximal end thereof for supporting a syringe in a fixed position; and
 c) first and second longitudinally spaced apart clamp holders operatively associated with the top surface of the platform, each clamp holder configured to support a respective vessel clamp, wherein the vessel clamps supported within the clamp holders are adapted to hold a harvested blood vessel immobile therebetween, providing temporary occlusion of the blood vessel after it has been inflated by a fluid from the syringe to allow for distention of the blood vessel so it can be prepared for grafting, wherein the first and second longitudinally spaced apart clamp holders are mounted for tandem movement within an elongated channel extending along the platform between the opposed proximal and distal end portions thereof.

2. The system as recited in claim 1, further comprising a syringe supported by the mounting flange for delivering fluid into a proximal end of the blood vessel held between the vessel clamps to inflate the blood vessel.

3. The system as recited in claim 2, wherein the mounting flange includes a reception slot and the system further comprises a funnel attached to a distal end of the syringe for engagement with the reception slot.

4. The system as recited in claim 1, wherein the clamp holders are supported on an elongated beam that is mounted for longitudinal movement on the platform within the elongated channel.

5. The system as recited in claim 4, wherein each clamp holder includes an arm that extends laterally outward from the elongated beam and includes a socket for receiving and retaining a respective vessel clamp.

6. The system as recited in claim 5, wherein each vessel clamp is a spring loaded bulldog clamp having a body portion configured for reception within the socket of each clamp holder.

7. The system as recited in claim 6, wherein each clamp holder has an associated fastener for retaining the body portion of a vessel clamp within the socket thereof.

8. A system for preparing a harvested blood vessel for grafting, comprising:
 a) an elongated platform;
 b) a mounting flange extending upwardly from a top surface of the platform adjacent a proximal end thereof for supporting a syringe in a fixed position;
 c) a syringe configured to be supported by the mounting flange for delivering fluid into a proximal end of the blood vessel;
 d) a pair of longitudinally spaced apart clamp holders operatively associated with the top surface of the platform, each clamp holder configured to support a respective vessel clamp; and
 e) a vessel clamp supported within each clamp holder for holding a harvested blood vessel immobile therebetween, providing temporary occlusion of the blood vessel after it has been inflated by fluid from the syringe to allow for distention of the blood vessel so it can be prepared for grafting, wherein the longitudinally spaced apart clamp holders are mounted for tandem movement within an elongated channel extending along the platform between the opposed proximal and distal end portions thereof.

9. The system as recited in claim 8, wherein the mounting flange includes a reception slot and the syringe includes a funnel attached to a distal end thereof for engagement with the reception slot.

10. The system as recited in claim 8, wherein the longitudinally spaced apart clamp holders are supported on an elongated beam that is mounted for longitudinal movement on the platform within the elongated channel.

11. The system as recited in claim 10, wherein each clamp holder includes an arm that extends laterally outward from the elongated beam and includes a socket for receiving and retaining a respective vessel clamp.

12. The system as recited in claim 8, wherein each vessel clamp is a spring loaded bulldog clamp having a body portion configured for reception within the socket of a clamp holder.

13. The system as recited in claim 12, wherein each clamp holder has an associated fastener for retaining the body portion of a vessel clamp within the socket thereof.

* * * * *